United States Patent [19]
Colon et al.

[11] Patent Number: 4,743,238
[45] Date of Patent: * May 10, 1988

[54] WETNESS INDICATING HOT-MELT ADHESIVES

[75] Inventors: Herman Colon, Monsey, N.Y.; Albery Maletsky, Franklin Lakes, N.J.

[73] Assignee: Malcolm Nicol & Co., Lyndhurst, N.J.

[*] Notice: The portion of the term of this patent subsequent to Jul. 21, 2004 has been disclaimed.

[21] Appl. No.: 70,206

[22] Filed: Jul. 14, 1987

Related U.S. Application Data

[63] Continuation-in-part of Ser. No. 839,943, Mar. 17, 1986, Pat. No. 4,681,576.

[51] Int. Cl.$^4$ .................... A61F 13/16; A61F 13/18; A61F 13/20; C08J 23/00
[52] U.S. Cl. .................... 604/361; 524/271; 524/272; 524/275; 524/322; 524/718; 524/378; 524/318; 524/310; 524/81; 523/111
[58] Field of Search ............... 524/271, 272, 275, 322, 524/718; 128/284, 287, 290 R; 604/361

[56] References Cited

U.S. PATENT DOCUMENTS

| | | | |
|---|---|---|---|
| 3,731,685 | 5/1973 | Eidas | 128/284 |
| 3,952,746 | 4/1976 | Summers | 128/287 |
| 4,231,370 | 11/1980 | Mroz et al. | 128/287 |
| 4,325,851 | 4/1982 | Colon et al. | 524/83 |
| 4,331,576 | 5/1982 | Colon et al. | 524/271 |
| 4,681,576 | 7/1987 | Colon et al. | 604/361 |

Primary Examiner—Harold D. Anderson
Attorney, Agent, or Firm—Erwin S. Teltscher

[57] ABSTRACT

A wetness indicating hot-melt adhesive which changes color in response to the presence of moisture is disclosed, which contains 20 to 70 wt. % of polymer, about 28 to 10 wt. % of which is water sensitive polymer; 25 to 60% of organic acid which is selected from a high acid fatty acid, or rosin acid, or a combination thereof; 0 to 40% of water soluble wax; 0 to 60 wt. % of glycerlo monostearate; 0 to 55 wt. % of hydrogenated castor oil; 0 to 15 wt. % of polyalkylene wax; 0 to 60 wt. % of compatible plasticizer; and a wetness indicating agent which changes the color of the composition in response to moisture therein. The time of response of the color change can be controlled from about one second to a somewhat larger value as desired.

45 Claims, No Drawings

WETNESS INDICATING HOT-MELT ADHESIVES

REFERENCE TO RELATED APPLICATIONS

This application is a continuation-in-part application of copending U.S. application Ser. No. 06/839,943 filed on Mar. 17, 1986, now U.S. Pat. No. 4,681,576.

FIELD OF THE INVENTION

This invention relates to wetness indicators. More specifically this invention concerns wetness indicating hot-melt adhesive compositions.

BACKGROUND OF THE INVENTION

Hot melt adhesives are well known. Generally, hot-melt adhesives are applied by melting the adhesive composition and applying a coat of the molten adhesive layer on a substrate. The coated material is then cooled to harden the adhesive layer and is ready for storage. Among the hot-melt adhesives that have been found useful and economically important are remoistenable hot-melt adhesives and remoistenable pressure-sensitive hot-melt adhesives.

Water activatable adhesives applied from water-based media are commonly used as envelope-flap adhesives, postage-stamp adhesives, binding tapes, sealing tapes, diapers and the like. Now, remoistenable hot-melt adhesives can be used for similar applications. For such use, it is desirable that the hot-melt coating be capable of storage without blocking, i.e. adhering due to activating of the adhesive by combination of ambient humidity, temperature and contact pressure. In addition, the dried adhesive, when contacted with water, must be uniformly activated and capable of developing an adherent bond between the coated surface and an uncoated surface. The hot-melt characteristics of the formulations are also important. The adhesive should have good pot life, at least 30–40 hours at usual application temperatures of about 350° F., as well as low viscosity characteristics at these temperatures, and the viscosity of the hot-melt should be substantially constant during the pot-life of the hot-melt.

As a result of previous work in this field, a water activatable adhesive which has excellent non-blocking and water activatable adhesive characteristics, and also excellent hot-melt characteristics has been found, as disclosed in U.S. Pat No. 4,325,851.

Pressure sensitive hot-melt adhesives are useful for the adhesive coating of labels, cloth patches and the like. A water soluble pressure-sensitive hot-melt adhesive composition with excellent adhesive properties has been disclosed in U.S. Pat. No. 4,331,576. Labels comprised of this water soluble pressure-sensitive hot-melt adhesive composition adhere permanently to substrates under normal conditions; on the other hand, when wet, such labels can be removed readily without damage to the substrate.

Non-pressure sensitive hot-melt adhesives have been used as the adhesive medium for multiline construction of disposable baby and adult diapers, sanitary napkins and hospital bed pads. In this construction the adhesive is applied in longitudinal, parallel or bead multi-lines to laminate a polyolefin film which forms the outer shell to tissues or non-woven substrates. It is often desirable to know if it is wet and thus a hot melt adhesive used in this capacity, and yet signaling the presence of water by a color change is invaluable.

An example of a non-pressure sensitive water based latex adhesive which when dry, signals the presence of water by a color change is taught in U.S. Pat. No. 4,231,370, issued to Mroz et al. According to this disclosure a flexible pH-change/color wetness indicator is coated on a surface portion of the product, which is visible through the cover member, and which retains sharp edge definition of the coated surface portion when wetted, for example, by urine. Such a coating includes a pH-change/color-change type material dispersed in a polymer latex matrix composed of styrene/2-ethylhexyl-acrylate copolymer, vinyl acetate/ethylene copolymer and polyvinyl acetate. To obtain a suitable pH, sufficient acid buffering means, such as phosphoric acid must be used; this is a harsh acid which could conceivably hurt a child.

It is a disadvantage of the broadly similar art, such as the Mroz et al composition, that the adhesive material can only be obtained by evaporation from a water-based latex composition. This means that equipment must be provided during the manufacture of the Mroz et al product which can release the water present. Also such problems as foaming, and proper wetting of the substrate must be overcome, all resulting in a more expensive manufacturing process of the Mroz et al formula. It is another disadvantage that any color change of the Mroz et al composition takes a very long time to take effect, e.g of the order of 3 minutes, as can be seen, for example, from FIGS. 3 and 4 of the Mroz et al patent.

Further, the time required for the color change in the Mroz et al composition is dependent on the thickness of the coating, as well as the pH of the wetting composition; the thicker the coating and the lower the pH, the slower the color change.

It is often desirable to know quickly, by visual inspection, whether a substrate has become wet. For example, it is desirable to know when a diaper has become set, but the wetness of a diaper which is plastic coated, or which is worn under a water proof panty, is not readily determined by visual inspection.

SUMMARY OF THE INVENTION

An object of the present invention is the provision of a hot-melt adhesive composition which is capable of indicating the presence of water therein.

Another object of the present invention is the provision of a hot-melt adhesive composition which changes color in response to wetness.

An important object of the present invention is the provision of a hot-melt adhesive composition which changes color in response to wetness with a controlled response time.

Still another object of the present invention is the provision of a hot melt adhesive composition which changes color in response to wetness, and wherein the response time can be controlled by varying the composition.

A further object of the present invention is the provision of a hot-melt adhesive which changes color rapidly when wet.

Another object of the present invention is the provision of a hot melt adhesive coating which changes color rapidly when wet, independent of the thickness of the coating and substantially independent of the pH of the wetting composition.

A particular object of the present invention is the provision of a hot-melt adhesive composition which is effective to show quickly that a diaper has become wet.

Another particular object of the present invention is the provision of a hot-melt adhesive composition which changes color in response to wetness on a substrate, and wherein the hot-melt adhesive composition has excellent pattern integrity when wet.

These and other objects are accomplished by the present invention.

A wetness indicating composition has been discovered which adheres substantially to any substrate, and which provides immediate recognition, by visual inspection, that the substrate has become wet.

According to the invention, the wetness indicating composition is composed of a hot-melt adhesive composition and a wetness indicating agent which causes the composition to change color in response to the presence of water in the composition.

The wetness indicating hot-melt adhesive composition of the invention comprises:

(A) 20 to 70 wt.% of total polymer components, said polymer components comprising about 28 to 100 wt.% of water sensitive polymer selected from vinyl pyrrolidone homopolymer, vinyl pyrrolidone/vinyl acetate copolymer or a mixture thereof, any balance compri-sing at least one polymer selected from the group consisting of ethylene vinyl acetate copolymer, ethylene/acrylic acid copolymer and polyamide;

(B) 25 to 60 wt.% of an acidic composition selected from
  (a) at least one free monobasic saturated or unsaturated fatty acid having an acid number above 137 or
  (b) at least one rosin acid having an acid number above 130; and
  (c) a combination of the free monobasic saturated or unsaturated fatty acid the the rosin acid;

(C) 0 to 40 wt.% of a water soluble wax; and (D) 0 to 60 wt. % of glycerol monostearate;

(E) 0 to 65 wt.% of hydrogenated castor oil;

(F) 0 to 15 wt.% of polyalkylene wax;

(G) 0 to 60 wt. % of compatible plasticizer; and (H) a wetness indicating agent capable of causing the composition to change color in response to the presence of moisture in the composition, in an amount effective to provide the composition with a readily visible color when wet, which is distinct from the color of the dry composition.

A further embodiment of the invention has the following composition:

(A) 20 to 70 wt.% of total polymer components, said polymer components comprising 35 to 100 wt.% of water sensitive polymer selected from vinyl pyrrolidone homopolymer, vinyl pyrrolidone/vinyl acetate copolymer or a mixture thereof, any balance comprising t least one polymer selected from the group consisting of ethylene vinyl acetate copolymer, ethylene/acrylic acid copolymer and polyamide;

(B) 27 to 60 wt.% of an acidic composition selected from
  (a) at least one free monobasic saturated or unsaturated fatty acid having an acid number above 137 or
  (b) 15 to 50 wt.% of the fatty acid in combination with 10 to 55 wt.% of at least one other organic acid having an acid number above 130;

(C) 0 to 30 wt.% of a water soluble wax; and (D) a wetness indicating agent capable of causing the composition to change color in response to the presence of moisture in the composition, in an amount effective to provide the composition with a readily visible color when wet, which is distinct from the color of the dry composition.

In a particular embodiment of the invention, a device, such as a label, tape, or plastic, which can be coated with a hot-melt, is coated with the wetness indicating hot-melt adhesive composition of the invention.

Another embodiment of the invention is a diaper which contains the wetness indicating hot-melt adhesive composition of the invention.

DETAILED DESCRIPTION AND PREFERRED EMBODIMENTS OF THE INVENTION

The polymer component of the wetness indicating hot-melt adhesive composition of the invention is based on water sensitive resin which is selected from vinyl pyrrolidone homopolymer (VP) and vinyl pyrrolidone/vinyl acetate copolymer (VP/VA) and mixtures thereof. In the copolymer, the proportion of the monomer components ranges from 3:1 to 1:3 by weight of each monomer moiety. Within this range the flow points of the copolymer are satisfactory for the hot-melt formulations of this invention.

A satisfactory copolymer in the solid state is marketed by GAF Corp. (NYC, N.Y., USA) under the trade name PVP/VA S630. This is a 60/40 VP/VA copolymer. Other polymers of different proportions are commercially available with most being marketed in solution form by GAF (USA) and BASF (W. Germany). A useful vinyl pyrrolidone homopolymer is marketed by BASF, under the tradename Luviskol. Products in solution form require removal of the solvents before or during the preparation of the hot-melt. The water sensitivity of these copolymers provides the water activatable or water sensitive property of the final adhesive formulation, when coated on the substrate.

Optionally, one or more additional polymers compatible with VP or VP/VA may be included in the adhesive composition of the invention. For example, ethylene/vinyl acetate copolymer (E/VA), ethylene/acrylic acid copolymer (E/AA) and polyamides (PA) are compatible with VP and VP/VA, and useful in the present formulations.

Such ethylene/vinyl acetate copolymers are marketed by several companies such as duPont (Delaware USA) under the "Elvax" trade name. The vinyl acetate content of these copolymers suitable for inclusion in the formulations of this invention ranges from about 17 to 29%. Preferred are the copolymers at the lower end of the range, as they are the most compatible with the VP/VA copolymers. The Elvax 410 series copolymer having a VA content of 17.5 to 18.5% is most preferred; it has a melt index (ASTM D 1238) of 455–550. E/VA copolymers produced by Allied Signal Corp., such as AC-400, are also suitable. The E/VA copolymer, unlike the VP/VA copolymer, is not water sensitive. It has been used as a major polymer component in direct sealing hot-melt adhesives, that is, in adhesives where the melt is applied and the surfaces joined before the melt solidifies.

Ethylene/acrylic acid copolymers suitable for use in the present compositions are produced by Allied Signal Co. under the Allied Signal trade name. Allied Signal Co. does not provide the copolymer ratios, but indicates the acid number to be between 40 and 75 for these specialty products.

The polyamide can be either of low amine number type (10–28) or of high acid number (80–140). The lower amine polyamide is produced by Emery Inc., while the high acid number polyamide is produced by Crosby Inc. of Los Angeles.

The total polymer content of the compositions of the invention may range from 20 to 70 wt.%, of which about 28 to 100 wt.%, and more preferably, about 35 to 100 wt. % is VP or VP/VA, and any remainder is selected from another polymer or copolymer such as E/VA, E/AA, PA and a combination thereof. It is also more preferable that the compositions of the invention contain about 30 to 65 wt.% of total polymer. In a particularly preferred embodiment at least 50 wt.% of the polymer components are VP/VA, VP, or a combination thereof.

However, desirable wetness indicating hot melt adhesives of the invention contain about 20 to 70 wt. % of polymer which is composed of (a) about 22 to 100 wt. % of VP or VP/VA and any balance; i.e. 0 to about 78 wt. % of E/AA, (b) about 2% to 100 wt. % pf VP or VP/VA, and any balance, i.e. 0 to about 72 wt. % E/VA and (c) about 28 to 100 wt. % of VP or VP/VA and any balance, i.e. 0 to about 72% of PA. It is generally preferred that VP or VP/VA be present in the compositions of the inventio in an amount of at least about 7 wt. % based on the total composition, and more preferably about 20 to 40 wt. %.

Fatty acids useful for the present invention are liquid or solid aliphatic branched or straight chain free fatty acids.

Other high acid number organic acides, i.e. organic acids having an acid number greater than 130, and particularly rosin acids, can be used alone or in combination with the fatty acids as the acidic components of the wetness indicating hot melt adhesive composition of the invention. Rosin acids include: tall oil rosin, such as Sylvatec 495 manufactured by Sylvachem; dimerized rosin, such as Dymerex, produced by Hercules, Inc; polymerized rosin, such as Poly-pale produced by Hercules Inc; saturated or hydrogenated rosin, such as Foral AX, manufactured by Hercules, Inc; partially hydrogenated rosin, such as Staybelite rosin, manufactured by Hercules, Inc., and disproportionated rosin, such as Arizona DR-22, manufactured by Arizona Chem. Co., Wayne, N.J.

Commercial liquid fatty acids may be blended with each other or with other high acid number organic acids including any of the types or rosin set forth above. The acids, when mixed, should be able to withstand 350° F. for 48 hrs., without any serious chemical degradation as evidenced by color or odor.

High acid number fatty acids, which contain at least 14 carbon atoms, when used alone, i.e. without other types of organic acids, may be present in an amount of 25 to 60 wt.%, depending on the desired characteristic of the adhesive. Alternatively, when used in combination with other high acid number organic acids, the fatty acids may be present in any amount to provide the necessary proportions of acid components in the composition; preferably the fatty acids are present an amount of about 15 to 50 wt.%, while the other organic acid make up the remaining acid requirements, i.e. about 10 to 45 wt.%.

When a pressure sensitive hot-melt adhesive is desired, it is preferable that the organic acid component be used in an amount of 27 to 60 wt.%, more preferably 35 to 50 wt.% of the composition. It is also preferable that the proportion of organic acid to total polymer in the composition be from 1:2 to 2:1. For example at a weight range of 13 or 14 wt.% of organic acid alone, the desired results are not achieved; a composition with this proportion of acid components is suitable as a remoistenable hot-melt adhesive only, but will not produce any change in color.

If desired, waxy materials selected from solid water soluble, waxy, polyethylene glycols of polyoxyethylene glycols (PEG) may be included in the wetness indicating adhesive composition of the invention in an amount up to about 40 wt.%, and more preferably up to about 30 wt. % to modify the physical properties of the composition. Commercial water soluble solid PEG waxes range in molecular weight from about 4,000 to about 20,000 and are marketed by Union Carbide under the Carbowax trade name; equivalent materials are available from other sources.

As the wetness indicating agent, a material which is compatible with the instant compositions, or VP and VP/VA polymers in particular, and which is capable of changing the color of the adhesive composition quickly when the adhesive composition is wet, compared to the color of the dry adhesive composition, may be used in the present wetness indicating adhesive composition. Acid-base indicators, which change color in response to a change in pH, are preferred, because they change color rapidly, and those providing a change to a bright, vivid color are generally most preferred. Other materials which change color in response to water may be used as the wetness indicating agent, such as dyes which are substantially invisible in the dry composition, which quickly become a vivid color when wet. An example of such a material is the blue dye Calcocid Blue 2G made by American Cyanamide Corp.

Acid-base indicators for use in the present compositions are those which change color at a pH in the range of about 3 to 7, such as Ethyl Red, Bromophenol Blue (made by Eastman Kodak), or Bromocresol Green mixed with Bromophenol Blue; Bromophenol Blue is particularly preferred. The wetness indicating agent is used in an amount effective to provide the composition with a readily visible color when the composition is wet, and of course, the readily visible color must be easily distinguishable from the color of the dry composition; generally about 0.05 to 0.1 wt.% pf indicator, based on the weight of the composition, is adequate.

Other compatible components which have a desired effect on the properties of the wetness indicating hot melt adhesive composition of the invention may be included therein. For example glycerol monostearate, such as Aldo 33 manufactured by Glyco Chemicals, Inc. can be included in the present composition in an amount of 0 to 60 wt. %, and more preferably 10 to 20 wt. % of the total composition to reduce the viscosity and thus provide for easier application of the composition to a substrate and to reduce tackiness. Hydrogenated castor oil, such as Castorwax, manufactured by Caschem Corp., Bayonne, N.J. is an effective compatibilizing aganet and a viscosity reducer which can be included in the composition of the invention in an amount of 0 to 55 wt. %, and more preferably 10 to 20 wt. % of the total composition. Polyalkyline waxes, including Fischer-Tropsch, polyethylene and ploymethylene wax can be included in an amount of 0 to 15 wt. %, and more preferably 5 to 10 wt. % of the compositions of the invention to improve high temperature resistance, and cold flow characteristics; further such waxes reduce water sensitivity and improve design integrity of a composition when contacted with moisture after having been applied to a substrate. Polyalkylene waxes include, for example, Bowax 1 manufactured by Boler Petroleum Co., Penna., Paraflint H 101, sold by Morre and Munger Co., N.Y., and Polywax, manufactured by Boreco, Tulsa, Okla.

Compatible plasticizer may also be included in the compositions of the invention in an amount of about 0 to 60 wt. %, more particularly about 0 to 25 wt. %. Solid plasticizers, such as Benzoflex 552, manufactured by Velsicol Co., improves cold flow properties and design integrity of the composition in contact with moisture after being applied to a substrate. Liquid plasticizers, such as Benzoflex 284 and Dantacol, manufactured by Glyco Chemicals, Inc., are useful in improving heat stability and viscosity stabilizers. In addition to liquid and solid plasticizers referred to above, triacetin, polyethylene glycols, citrates, phthalates and other compatible plasticizers, which are readily apparent to those skilled in the art as useful in combination with the required components of the composition, can be included.

Further optional components of the compositions of the invention include antioxidants, which may be added in an amount of about 0.05 to 0.1 wt.%, rosins, such as Sylvatac 95, (made by Sylvachem Corp.), plasticizer, such as Dantocol, surfactants, essential oils and perfumes and similar special purpose additives common in this art, and are within the ambit of the invention.

The response time to the presence of moisture of the composition of the invention can be controlled by varying the components of the composition, particularly polyalkylene wax and high temperature melting rosin acids, which, although increasing the response time, increase pattern integrity and improve cold flow. However, increased pattern integrity and improved cold flow can also be achieved without increasing the response time by including solid plasticizer in the composition.

Compared to compositions of the prior art, color change in the composition, according to the present invention, can be very fast, and substantially independent of the thickness of the composition of the coating applied to a substrate and of pH range within certain limits of the wetting composition. Thus a change in color can be obtained within 5-30 seconds. This can be even faster, i.e. substantially instantaneous, depending of the shape of the beadline. On the other hand, if desired, the response time can be increased to 3 minutes or more by varying the formulation as set forth above, and in the examples which follow.

The following examples of the invention are for the purpose of illustrating representative compositions preferred for specific uses, and it must be realized that no single formulation is satisfactory for all substrates. All proportions are by weight unless otherwise indicated.

EXAMPLE 1

The antioxidant, Irganox 1010 (manufactured by Ciba-Geigy) in an amount of 0.1 wt.% and about 0.05 wt.% Bromophenol Blue were mixed with the other nonpolymer components until uniform, with heating and then the polymer was added with continued heating at a temperature of about 160°-177° C. with stirring until dissolved.

The proportion of fatty acid and polymer components was as follows:
Fatty acid (Emersol 871): 36 wt.%
Ethylene/acrylic acid copolymer (AC-580): 18 wt.%
Vinyl pyrrolidine/vinyl acetate copolymer PVP-VA S630, mfg. by GAF Corp. to mak up: 100 wt.%

This adhesive product can be applied to a substrate, such as a polyethylene film, in an amount sufficient to cause the polyethylene film to adhere to another substrate, such as absorbent, non-woven material. When the absorbent material is wet, the adhesive product immediately turns bright blue.

EXAMPLES 2-6

These examples have been prepared as described in Example 1, and contain 0.1 wt.% of the antioxidant, Irganox 1010, 0.07 wt.% of the pH indicator Bromophenol Blue, as well as polymer, water soluble wax, and fatty acid in the amounts in wt. % shown in Table 1.

In these examples the following materials have been used.
Polymer: PVP-VA S630; vinyl pyrrolidone/vinyl acetate copolymer
Fatty acid:
Emersol 871 in Examples 2-4 and 6
Emersol 150 in Example 5
Water soluble wax: Carbowax 4000

TABLE 1

| Component | EXAMPLE | | | | |
|---|---|---|---|---|---|
| | 2 | 3 | 4 | 5 | 6 |
| Polymer | 40 | 40 | 54.6 | 54.6 | 20.0 |
| Fatty acid | 50 | 40 | 27.3 | 27.3 | 53.3 |
| Water sol. wax | 10 | 20 | 18.1 | 18.1 | 26.7 |

The hot-melt of examples 2-5 forms an adhesive film on a substrate such as paper, polyethylene or polypropylene, which is light yellow in color. When wet, the film turns bright blue immediately. Example 6 is a light yellow gel, which changes to a bright blue color in response to wetness.

EXAMPLE 7

In combination with 0.1 wt.% of the antioxidant, Irganox 1010 and 0.07 wt.% of Bromophenol Blue, the following components were mixed under the conditions described in Example 1.
Pyrrolidone homopolymer (Luviskol K-30): 30.00 wt.%
Ethylene/vinyl acetate copolymer (Elvax 410): 20.00 wt.%
High acid no cpd., i.e. fatty acid (Emersol 871) to make up: 100.00 wt.%

This product forms an adherent film, light yellow in color, on a substrate such as paper, polyethylene, or polypropylene, which turns bright blue immediately when wet with water.

EXAMPLES 8-10

The formulation in Table 2, in wt. %, plus 0.1 wt.% of the antioxidant Irganox 1010 and 0.07 wt. % of the pH indicator, Bromophenol blue, yield products which form light yellow colored, adherent films on substrates such as paper, polyethylene, polyester non-woven fibers, and polypropylene. The films are effective to cause the substrate to adhere to another material, and become bright blue in color in response to contact with a wet paper towel.

TABLE 2

| Component | EXAMPLE 8 | EXAMPLE 9 | EXAMPLE 10 |
|---|---|---|---|
| Vinyl pyrrolidone/vinyl acetate copolymer (PVP-VA S30) | 40 | 36.3 | 45.5 |
| Ethylene/vinyl acetate copolymer (Elvax 410) | 10 | 18.2 | 18.2 |
| Fatty acid (Emersol 871) | 50 | 45.5 | 36.3 |

EXAMPLES 11–13

The formulations in wt. % shown in table 3 were each combined with 0.1% of the antioxidant Irganoz 1010 and 0.07% of Bromophenol Blue. Each of the resultant compositions formed an adherent film on paper and plastic substrate which turned blue in the presence of moisture.

TABLE 3

| Component | EXAMPLE 11 | EXAMPLE 12 | EXAMPLE 13 |
|---|---|---|---|
| Fatty acid (Emersol 871) | 40.00 | 40.00 | 40.00 |
| Ployamide (Unirez 1530) mfg. by Union Camp. Co. | 15.00 | 0.00 | 0.00 |
| Hydrogenated rosin acid (FORAL AX) mfg. by Hercules Inc. | 0.00 | 20.00 | 0.00 |
| Tall oil rosin acid (SYLVATEC 495) mfg. by Sylvachem | 0.00 | 0.00 | 20.00 |
| PVP-VA S630 | 45.00 | 40.00 | 40.00 |

The composition of example 11 changes color substantially instantaneously in the presence of moisture.

The composition of example 12 has particularly good thermal stability due to the presence of hydrogenated rosin. Example 13 illustrates a composition of the invention containing tall oil rosin.

EXAMPLES 14–16

The formulations in wt. % set forth in table 4 were each combined with 0.1 wt. % of Irganox and 0.07% of Bromophenol Blue; a composition was obtained, which could be applied as an adherent film on a substrate, such as paper and plastic, and which turned bright blue in the presence of moisture.

TABLE 4

| Component | EXAMPLE 14 | EXAMPLE 15 | EXAMPLE 16 |
|---|---|---|---|
| Fatty acid (Emersol 871) | 10.00 | 0.00 | 10.00 |
| Liquid plasticizer (Benzoflex 284) mfg. by Velsicol Co. | 0.00 | 0.00 | 5.00 |
| Solid Plasticizer (Benzoflex 552) | 20.00 | 25.00 | 15.00 |
| Hydrogenated rosin (FORAL AX) mfg. by Hercules, Inc. | 35.00 | 35.00 | 35.00 |
| E/VA copolymer (AC-400) mfg. by Allied signal | 5.00 | 10.00 | 5.00 |
| VP/VA copolymer (PVP-VA S630) | 30.00 | 30.00 | 30.00 |

The compositions of examples 14, 15 and 16 have very good cold flow properties and the moistened compositions have excellent design integrity due to the inclusion of a solid plasticizer.

Example 15 illustrates a composition of the invention wherein the acid component is provided solely by rosin acid.

The compositions illustrated in examples 14–16 illustrate the use of AC400 a lower molecular weight E/VA copolymer.

EXAMPLES 17–20

The formulations in wt. % shown in table 5 were each combined with 0.1% of Irganoz 1010 and 0.07 wt. % of Bromophenol Blue. Each of the resultant compositions formed and adherent film on a substrate including paper and plastic, which turned bright blue in the presence of moisture.

TABLE 5

| Component | EXAMPLE 17 | EXAMPLE 18 | EXAMPLE 19 | EXAMPLE 20 |
|---|---|---|---|---|
| Fatty acid (Emersol 871) | 25.00 | 25.00 | 12.50 | 0.00 |
| Fatty acid (Emersol 150) | 0.00 | 0.00 | 0.00 | 5.00 |
| Plasticizer (Benzoflex 284) | 0.00 | 0.00 | 12.50 | 20.00 |
| Hydrogenated rosin acid (FORAL AX) | 25.00 | 25.00 | 35.00 | 23.00 |
| Dimerized rosin acid (Dymerex) | 0.00 | 0.00 | 0.00 | 12.50 |
| E/VA copolymer (Elvax 410) | 0.00 | 0.00 | 7.50 | 0.00 |
| Glycerol monostearate (Aldo MS) | 20.00 | 0.00 | 0.00 | 8.00 |
| Polyalkylene wax (Bowax 1) | 0.00 | 0.00 | 0.00 | 7.00 |
| Hydrogenated Castor oil (Castorwax) mfg. by Caschem Oil Co. | 0.00 | 20.00 | 0.00 | 0.00 |
| VP/VA copolymer (PVP-VA S60) | 30.00 | 30.00 | 33.00 | 25.00 |

In examples 17–19 where a liquid fatty acid is included in the formulations, the resultant compositions have low viscosity, whereas the use of a solid fatty acid in example 20 produces a composition of higher viscosity. Glycerol monostearate is a viscosity control agent which has been used in the compositions of examples 17 and 20 for this purpose. The presence of liquid plasticizer in the compositions of examples 19 and 20 provides improved thermal stability and lower viscosity, while the inclusion of hydrogenated castor oil in example 18 provides a composition with a higher softening point and better cold flow characteristics. Example 20 illustrates a composition with a longer response time of about 3–5 minutes for a coating of the composition of 1.5 mils, and excellent pattern integrity, when the composition is applied to a substrate and then moistened.

Tests of the response time of a composition of the invention having the following formulation in wt. % were carried out:

| | % |
|---|---|
| Pyrrolidone/acetate copolymer (PVP 630, GAF) | 45.45 |
| Isostearic acid (Emersol 875 - Emery Industries) | 45.45 |
| Polyamide resin (Univez 1530 Emery Industries) | 9.10 |
| | 100.00 |
| Irganox 1010 | is 0.1% on Batch |
| Bromophenol Blue | is 0.075% on Batch |

Tests were carried out on films useful for commercial applications as set forth below.

TABLE 6

| Film thickness (inches) | Time for color change (seconds) |
|---|---|
| 0.00025 (0.25 mils) | 1 (substantially instantaneous) |
| 0.00080 (0.80 mils) | 5–7 |
| 0.00180 (1.80 mils) | 10–15 |

TABLE 6-continued

| Film thickness (inches) | Time for color change (seconds) |
|---|---|
| 0.00235 (2.35 mils) | 18–20 |

From the results set forth in table 6 it is evident that a wetness indicating hot melt adhesive of the invention can have an exceedingly fast response time in the presence of wetness, i.e. within about 1–20 seconds.

What we desire to claim and protect by Letters Patent is:

1. A wetness indicating hot-melt adhesive composition comprising:
   (A) 20 to 70 wt.% of total polymer components, said polymer components comprising about 28 to 100 wt.% of water sensitive polymer selected from vinyl pyrrolidone homopolymer, vinyl pyrrolidone/vinyl acetate copolymer, or a mixture thereof, any balance comprising at least one polymer selected from the group consisting of ethylene/vinyl acetate copolymer, ethylene/acrylic acid copolymer and polyamide;
   (B) 25 to 60 wt. % of an acidic composition selected from the group consisting of
      (a) at least one free monobasic saturated or unsaturated fatty acid having an acid number above 137,
      (b) at least one rosin acid having an acid number above 130, and
      (c) a combination of said free monobasic saturated or unsaturated fatty acid and said rosin acid;
   (C) 0 to 40 wt.% of water soluble wax;
   (D) 0 to 60 wt.% of glycerol monostearate;
   (E) 0 to 55 wt.% of hydrogenated castor oil;
   (F) 0 to 15 wt.% of polyalkylene wax;
   (G) 0 to 60 wt.% of compatible plasticizer; and
   (H) a wetness indicating agent capable of causing the composition to change color in response to the presence of moisture, in an amount effective to provide the composition with a readily visible color when wet, which is distinct from the color when dry.

2. The wetness indicating hot-melt adhesive composition according to claim 1, wherein said composition contains at least about 7 wt.% of said water sensitive polymer.

3. The wetness indicating hot-melt adhesive composition according to claim 1, wherein said composition contains at least about 20 to 40 wt.% of said water sensitive polymer.

4. The wetness indicating hot-melt adhesive composition according to claim 1, which contains 25 to 60 wt.% of at least one free monobasic saturated or unsaturated fatty acid having an acid number above 137.

5. The wetness indicating hot-melt adhesive composition according to claim 1, which contains 25 to 60 wt.% of at least on rosin acid having an acid number above 130.

6. The wetness indicating hot-melt adhesive composition according to claim 1, which contains 25 to 60 wt.% of a combination of said free monobasic saturated or unsaturated fatty acid and said rosin acid.

7. The wetness indicating hot-melt adhesive composition according to claim 1, in which the proportion of said acidic composition in the composition is such that the pH of the composition, when wet, is in the range of 2 to 14.

8. The wetness indicating hot-melt adhesive composition according to claim 1, in which the ratio by weight of the acidic composition to the total polymer components is about 1:2 to 2:1.

9. The wetness including hot-melt adhesive composition according to claim 7, in which the wetness indicating agent is an acid-base indicator which changes color at a pH within the range of about 2 to 14.

10. The wetness indicating hot-melt adhesive composition according to claim 1, in which the wetness indicating agent is Bromophenol Blue.

11. The wetness indicating hot-melt adhesive composition according to claim 1, in which the composition changes color rapidly in response to the presence of moisture.

12. The wetness indicating hot-melt adhesive composition according to claim 1, wherein said water soluble wax comprises polyoxyethylene glycol.

13. The wetness indicating hot-melt adhesive composition according to claim 1, wherein said wetness indicating agent comprises Bromophenol Blue and said water soluble wax comprises polyoxyethylene glycol.

14. The wetness indicating hot-melt adhesive composition according to claim 1, which contains 5 to 25 wt.% of water soluble wax.

15. The wetness indicating hot-melt adhesive composition, according to claim 1, which contains 10 to 20 wt.% of water soluble wax.

16. The wetness indicating hot-melt adhesive composition according to claim 1, which contains about 5 to 20 wt.% of glycerol monostearate.

17. The wetness indicating hot-melt adhesive composition according to claim 1, which contains about 5 to 15 wt.% of hydrogenated castor oil.

18. The wetness indicating hot-melt adhesive composition according to claim 1, which contains about 5 to 10 wt.% of polyalkylene wax.

19. The wetness indicating hot-melt adhesive composition according to claim 1, which contains about 0 to 25 wt.% of compatible plasticizer.

20. An article comprising a substrate and a coating of the wetness indicating hot-melt adhesive composition according to claim 1 on at least one surface of the substrate.

21. An article according to claim 20, wherein the coating is a foil substrate.

22. A diaper comprising a moisture absorbent substrate, a water resistant covering for said absorbent substrate and the wetness indicating hot-melt adhesive composition according to claim 1 coated on at least a portion of an inner surface of the water resistant covering.

23. A wetness indicating hot-melt adhesive composition comprising:
   (A) 20 to 70 wt.% of total polymer components, said polymer components being selected from
      (a) about 22 to 100 wt.% water sensitive polymer selected from vinyl pyrrolidone homopolymer, vinyl pyrrolidone/vinyl acetate copolymer, or a mixture thereof, and 78 to 0 wt.% of ethylene/acrylic acid copolymer,
      (b) about 28 to 100 wt.% of water sensitive polymer selected from vinyl pyrrolidone homopolymer, vinyl pyrrolidone/vinyl acetate copolymer, or a mixture thereof, and 72 to 0 wt.% of ethylene/vinyl acetate copolymer, and
      (c) about 28 to 100 wt.% of water sensitive polymer selected from vinyl pyrrolidone homopolymer, vinyl pyrrolidone/vinyl acetate copolymer, or a mixture thereof, and 72 to 0 wt.% of polyamide;
(B) 25 to 60 wt.% of an acidic composition selected from the group consisting of
  (a) at least one free monobasic saturated or unsaturated fatty acid having an acid number above 137,
  (b) at least one rosin acid having an acid number above 130, and
  (c) a combination of said free monobasic saturated or unsaturated fatty acid and said rosin acid;
(C) 0 to 40 wt.% of water soluble wax;
(D) 0 to 60 wt.% of glycerol monostearate;
(E) 0 to 55 wt.% of hydrogenated castor oil;
(F) 0 to 15 wt.% of polyalkylene wax;
(G) 0 to 55 wt.% of compatible plasticizer; and
(H) a wetness indicating agent capable of causing the composition to change color in response to the presence of moisture, in an amount effective to provide the composition with a readily visible color when wet, which is distinct from the color when dry.

24. The wetness indicating hot-melt adhesive composition according to claim 23, in which the polymer components are comprised of about 22 to 100 wt.% water sensitive polymer selected from vinyl pyrrolidone homopolymer, vinyl/pyrrolidone/vinyl acetate copolymer, or a mixture thereof, and 78 to 0 wt.% comprising ethylene/acrylic acid copolymer.

25. The wetness indicating hot-melt adhesive composition according to claim 23, in which the polymer components are comprised at about 28 to 100 wt.% of water sensitive polymer selected from vinyl pyrrolidone homopolymer, vinyl pyrrolidone/vinyl acetate copolymer, or a mixture thereof, and 72 to 0 wt.% of ethylene/vinyl acetate copolymer.

26. The wetness indicating hot-melt adhesive composition according to claim 23, in which the polymer components are comprised of about 28 to 100 wt.% of water sensitive polymer selected from vinyl pyrrolidone homopolymer, vinyl pyrrolidone/vinyl acetate copolymer, or a mixture thereof, and 72 to 0 wt.% of polyamide.

27. The wetness indicating hot-melt adhesive composition according to claim 23, wherein said composition contains at least about 7 wt.% of said water sensitive polymer.

28. The wetness indicating hot-melt adhesive composition according to claim 23 which contains 25 to 60 wt.% of at least one free monobasic saturated or unsaturated fatty acid having an acid number above 137.

29. The wetness indicating hot-melt adhesive composition according to claim 23, which contains 25 to 60 wt.% of at least one rosin acid having an acid number above 130.

30. The wetness indicating hot-melt adhesive composition according to claim 23, which contains 25 to 60 wt.% of a combination of said free monobasic saturated or unsaturated fatty acid and said rosin acid.

31. The wetness indicating hot-melt adhesive composition according to claim 23, in which the proportion of said acidic composition in the composition is such that the pH of the composition, when wet, is in the range of 3 to 11.

32. The wetness indicating hot-melt adhesive composition according to claim 23 in which the ratio by weight of the acidic composition to the total polymer components is about 1:2 to 2:1.

33. The wetness indicating hot-melt adhesive composition according to claim 28, in which the wetness indicating agent is an acid-base indicator which changes color at a pH within the range of about 3 to 11.

34. The wetness indicating hot-melt adhesive composition according to claim 23, in which the composition changes color rapidly in response to the presence of moisture.

35. The wetness indicating hot-melt adhesive composition according to claim 23, wherein said water soluble wax comprises polyoxyethylene glycol.

36. The wetness indicating hot-melt composition according to claim 23, wherein said wetness indicating agent comprises Bromophenol Blue and said water soluble wax comprises polyoxyethylene glycol.

37. The wetness indicating hot-melt adhesive composition according to claim 23, which contains 5 to 25 wt.% of water soluble wax.

38. The wetness indicating hot-melt adhesive composition according to claim 23, which contains 10 to 20 wt.% of water soluble wax.

39. The wetness indicating hot-melt composition according to claim 23, which contains about 5 to 20 wt.% of glycerol monostearate.

40. The wetness indicating hot-melt adhesive composition according to claim 23, which contains about 5 to 15 wt.% of hydrogenated castor oil.

41. The wetness indicating hot-melt adhesive composition according to claim 23, which contains about 5 to 10 wt.% of polyalkylene wax.

42. The wetness indicating hot-melt adhesive composition according to claim 23, which contains about 0 to 25 wt.% of compatible plasticizer.

43. An article comprising a substrate and a coating of the wetness indicating hot-melt adhesive composition according to claim 23 on at least one surface of the substrate.

44. An article according to claim 43, wherein the coating is a foil substrate.

45. A diaper comprising a moisture absorbent substrate, a water resistant covering for said absorbent substrate and the wetness indicating hot-melt adhesive composition accordig to claim 23 coated on at least a portion of an inner surface of the water resistant covering.

* * * * *